(12) United States Patent
DeSanti

(10) Patent No.: US 8,167,612 B2
(45) Date of Patent: May 1, 2012

(54) METHOD FOR REMOVING AN ORTHODONTIC ALIGNER WITH A REMOVAL TOOL

(76) Inventor: Michael F. DeSanti, Huntington Station, NY (US)

( * ) Notice: Subject to any disclaimer, the term of this patent is extended or adjusted under 35 U.S.C. 154(b) by 341 days.

(21) Appl. No.: 12/545,814

(22) Filed: Aug. 22, 2009

(65) Prior Publication Data

US 2011/0045427 A1 Feb. 24, 2011

(51) Int. Cl.
*A61C 3/00* (2006.01)
(52) U.S. Cl. ............................... 433/3; 433/6; 433/141
(58) Field of Classification Search .................. 433/3, 4, 433/141, 6; 132/329; 7/151, 156; 81/3.55, 81/3.57
See application file for complete search history.

(56) References Cited

U.S. PATENT DOCUMENTS

| | | | |
|---|---|---|---|
| 1,520,670 A * | 12/1924 | Appel | 7/156 |
| 4,904,183 A | 2/1990 | Hannan et al. | |
| 5,242,302 A | 9/1993 | Riehm | |
| 5,538,421 A * | 7/1996 | Aspel | 433/4 |
| 5,820,368 A | 10/1998 | Wolk | |
| 7,011,517 B2 | 3/2006 | Nicozisis | |
| 2001/0031444 A1 * | 10/2001 | Cozzi | 433/141 |
| 2008/0160473 A1 * | 7/2008 | Li et al. | 433/3 |
| 2009/0258323 A1 * | 10/2009 | Saubers | 433/6 |

OTHER PUBLICATIONS

Printout of http://www.outietool.com/ (Jul. 29, 2009).
Printout of http://www.dentakit.com/rereto.html, pp. 1-2 (Jul. 29, 2009).

* cited by examiner

*Primary Examiner* — John J Wilson
(74) *Attorney, Agent, or Firm* — Ido Tuchman

(57) ABSTRACT

An orthodontic aligner removal tool, kit, and method of using the same. An embodiment of the tool includes a shaft including a proximate end and a distal end. A C-shaped portion is positioned at the proximate end of the shaft. The C-shaped portion includes a top hook and a bottom hook. The top hook extends from the shaft and curves toward the bottom hook. The bottom hook extends from the shaft and curves toward the top hook. A handle portion is positioned at the distal end of the shaft.

1 Claim, 6 Drawing Sheets

METHOD FOR REMOVING AN ORTHODONTIC ALIGNER WITH A REMOVAL TOOL

BACKGROUND OF THE INVENTION

1. Field of the Invention

The present invention relates to orthodontics, and, more particularly, an orthodontic aligner removal tool.

2. Description of Background

Orthodontic devices are commonly used to slowly realign misaligned or crooked teeth. These devices include orthodontic aligners (referred to herein as "aligners" or "orthodontic aligners") made from a hard, plastic material.

Treatment using orthodontic aligners includes a set of aligners fabricated to tightly fit over the patient's teeth. Typically, each aligner in the set is designed to inclemently move the patient's teeth a little closer to their final position. Thus, each aligner is slightly different than the next aligner in the set. An individual's orthodontic treatment may require aligner use over the span of years, depending on the severity of teeth misalignment.

The orthodontist or dentist will typically attach small brackets on the patient's teeth which can help hold the aligners in place once seated properly. Patients are often given something to bite down on to securely set the aligners onto the teeth. This could be a common cotton roll or a soft rubbery material.

Generally, patients are instructed to replace their current aligner with the next successive aligner in the set approximately every two weeks. Thus, a patient generally replaces his or her orthodontic aligners many times throughout treatment.

Patients may also be instructed to remove their aligners before eating or drinking fluids (except water). Beyond eating and drinking, patients may have a number of reasons to remove their aligners. These reasons include difficulty speaking, cosmetic purposes, brushing teeth, and mouth pain. Thus, a user may remove and insert his or her aligners several times throughout the day.

However, due to the aligners having such an exact fit over the user's teeth, it can be very difficult and frustrating for patients to remove the aligners with their fingers. Patients often resort to prying aligners off their teeth with crochet hooks or other sharp household objects when attempting to remove tightly fitting aligners. Patients may carry these unhygienic and potentially injurious items with them throughout the day in their pockets or purses.

SUMMARY OF THE INVENTION

The present invention includes an orthodontic aligner removal tool to assist a patient in treatment to remove their aligners as needed or desired. The orthodontic aligner removal tool may allow for one or more specified locations on which to connect a bite set device to assist in inserting the aligners in the patient's mouth. This will allow for a safer, more hygienic technique in tightly fitting the aligners.

The orthodontic aligner removal tool can allow a patient to remove the aligners quickly, safely and more sanitarily than the general practiced method of using hands or other household items. The orthodontic aligner removal tool offers a patient the ease of convenience to efficiently remove and set their aligners as needed or desired.

One aspect of the invention is an orthodontic aligner removal tool including a shaft, a C-shaped portion and a handle. The shaft includes a proximate end and a distal end. The C-shaped portion is positioned at the proximate end of the shaft. The C-shaped portion includes a top hook and a bottom hook. The top hook extends from the shaft and curves toward the bottom hook. The bottom hook extends from the shaft and curves toward the top hook. The handle portion is positioned at the distal end of the shaft.

Another aspect of the invention is an orthodontic appliance kit. The kit includes a case, at least one orthodontic aligner for aligning teeth of a patient positioned inside the case, and an aligner removal tool positioned inside the case. The orthodontic aligner removal tool includes a shaft, a C-shaped portion and a handle. The shaft includes a proximate end and a distal end. The C-shaped portion is positioned at the proximate end of the shaft. The C-shaped portion includes a top hook and a bottom hook. The top hook extends from the shaft and curves toward the bottom hook. The bottom hook extends from the shaft and curves toward the top hook. The handle portion is positioned at the distal end of the shaft.

Yet another aspect of the invention is a method for removing an orthodontic aligner seated on an upper set of teeth and lower set of teeth. The method includes an inserting step for inserting a removal tool into a mouth. The removal tool includes a C-shaped portion having a top hook and a bottom hook. The top hook extends from a shaft and curves toward the bottom hook. The bottom hook extends from the shaft and curves toward the top hook.

A placing step places a portion of the top hook between the orthodontic aligner and the upper set of teeth. An advancing step advances the removal tool toward the lower set of teeth after placing the portion of the top hook between the orthodontic aligner and the upper set of teeth until the orthodontic aligner is unseated from the upper set of teeth.

Another placing step places a portion of the bottom hook between the orthodontic aligner and the lower set of teeth. Another advancing step advances the removal tool toward the upper set of teeth after placing the portion of the bottom hook between the orthodontic aligner and the lower set of teeth until the orthodontic aligner is unseated from the lower set of teeth.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION OF THE INVENTION

Figure 1:
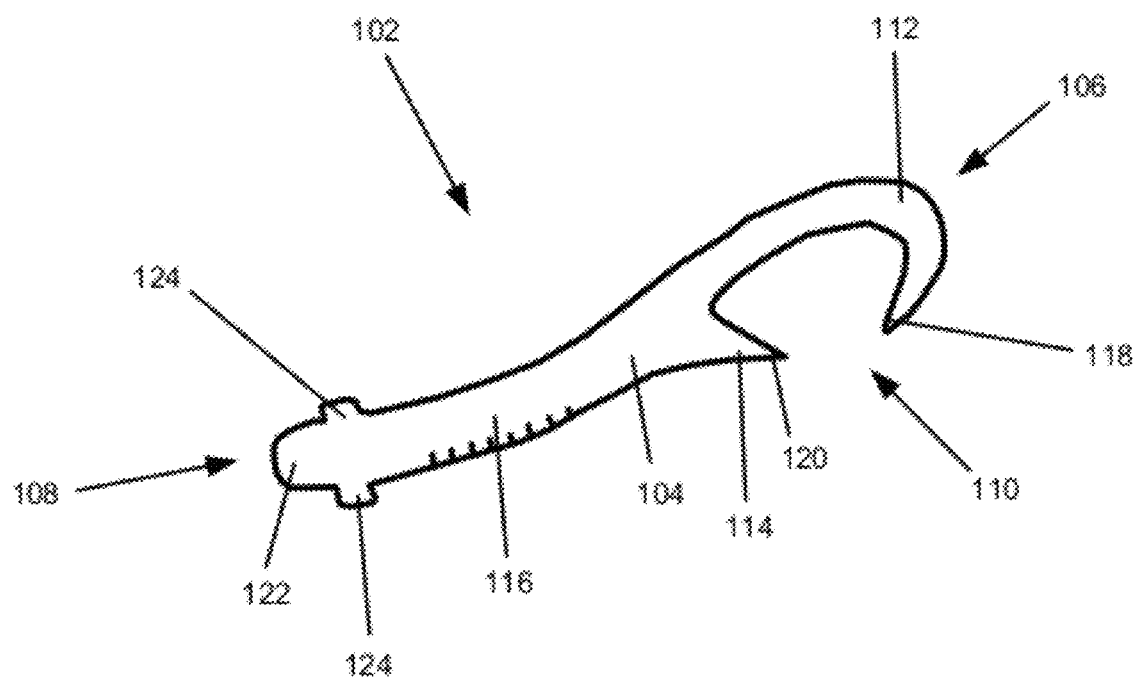
FIG. 1 shows an example aligner removal tool contemplated by the present invention.
Figure 2:
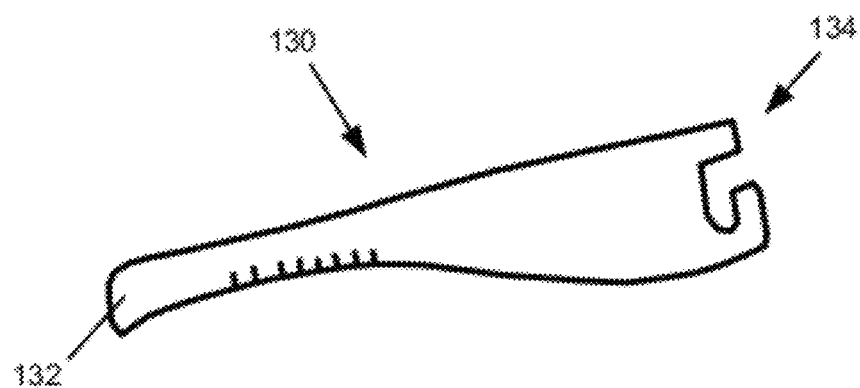
FIG. 2 shows an example extension handle configured to attach to the handle portion of the aligner removal tool.
Figure 3:
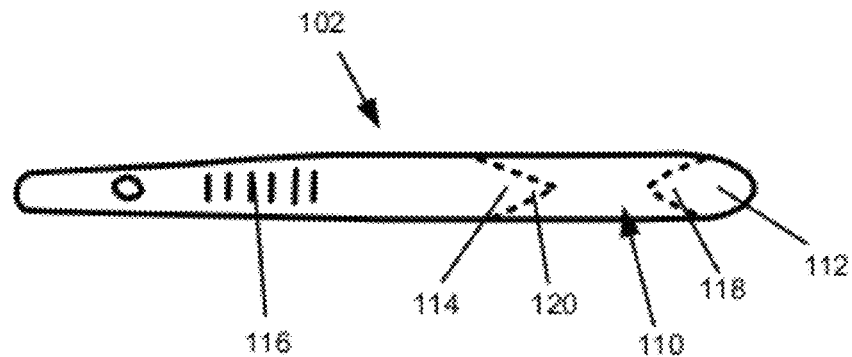
FIG. 3 shows a top view of the aligner removal tool.
Figure 4:
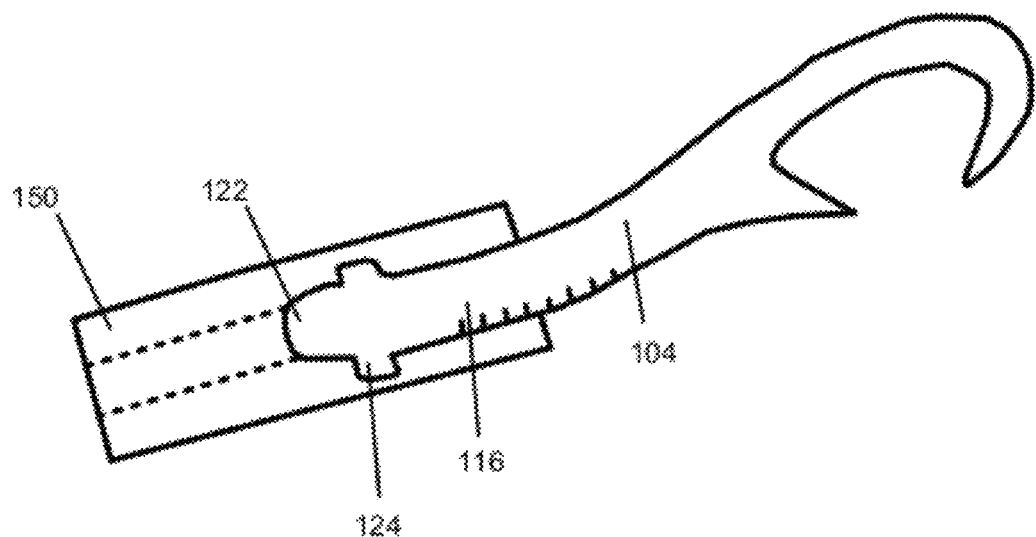
FIG. 4 shows a cross sectional view of a flexible sleeve attached to the handle portion of the aligner removal tool.
Figure 5:
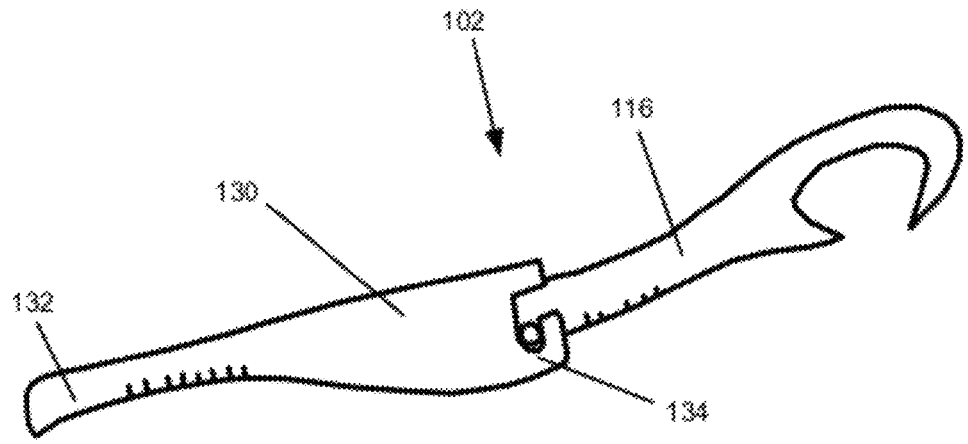
FIG. 5 shows the extension handle attached to the handle portion of the aligner removal tool.
Figure 6:
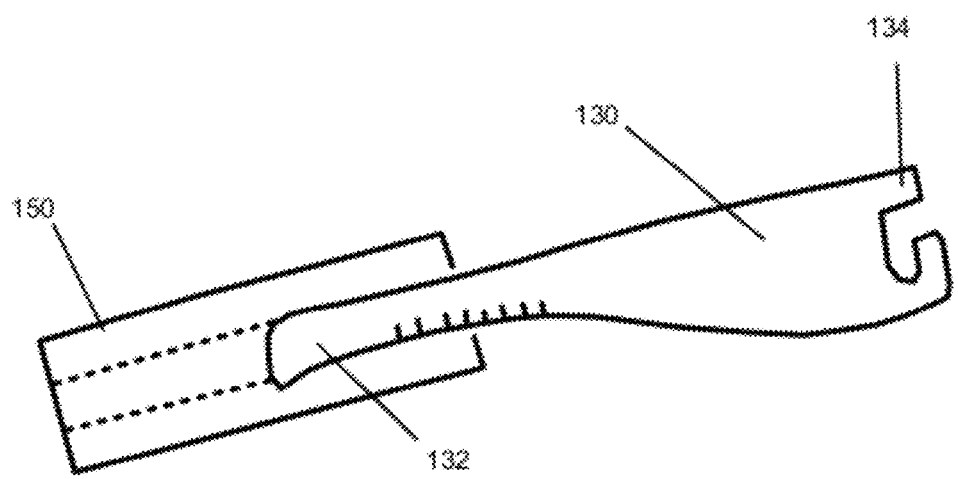
FIG. 6 shows a cross sectional view of a flexible sleeve attached to a tapered end of the extension handle.
Figure 7:
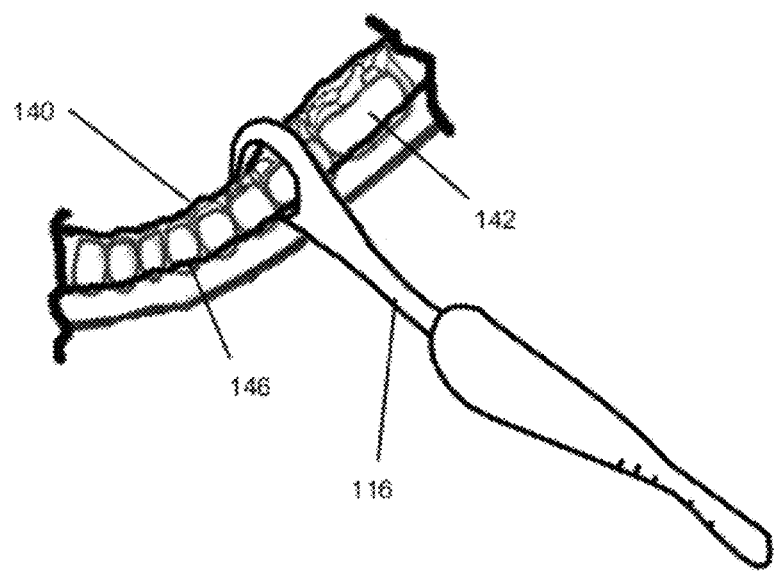
FIG. 7 shows a bottom hook of the aligner removal tool engaged between with a bottom aligner and a bottom set of teeth.
Figure 8:
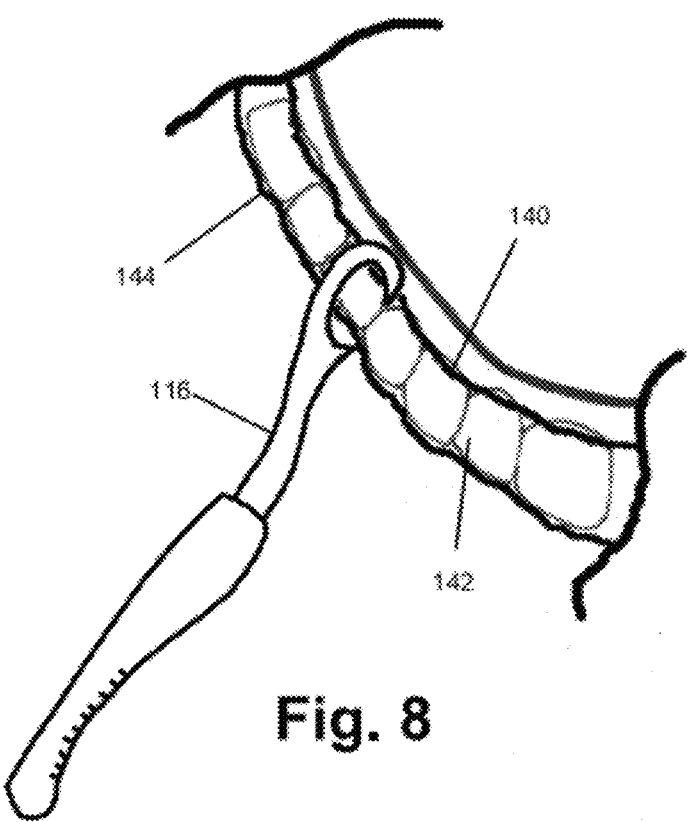
FIG. 8 shows a top hook of the aligner removal tool engaged between with a top aligner and a top set of teeth.
Figure 9:
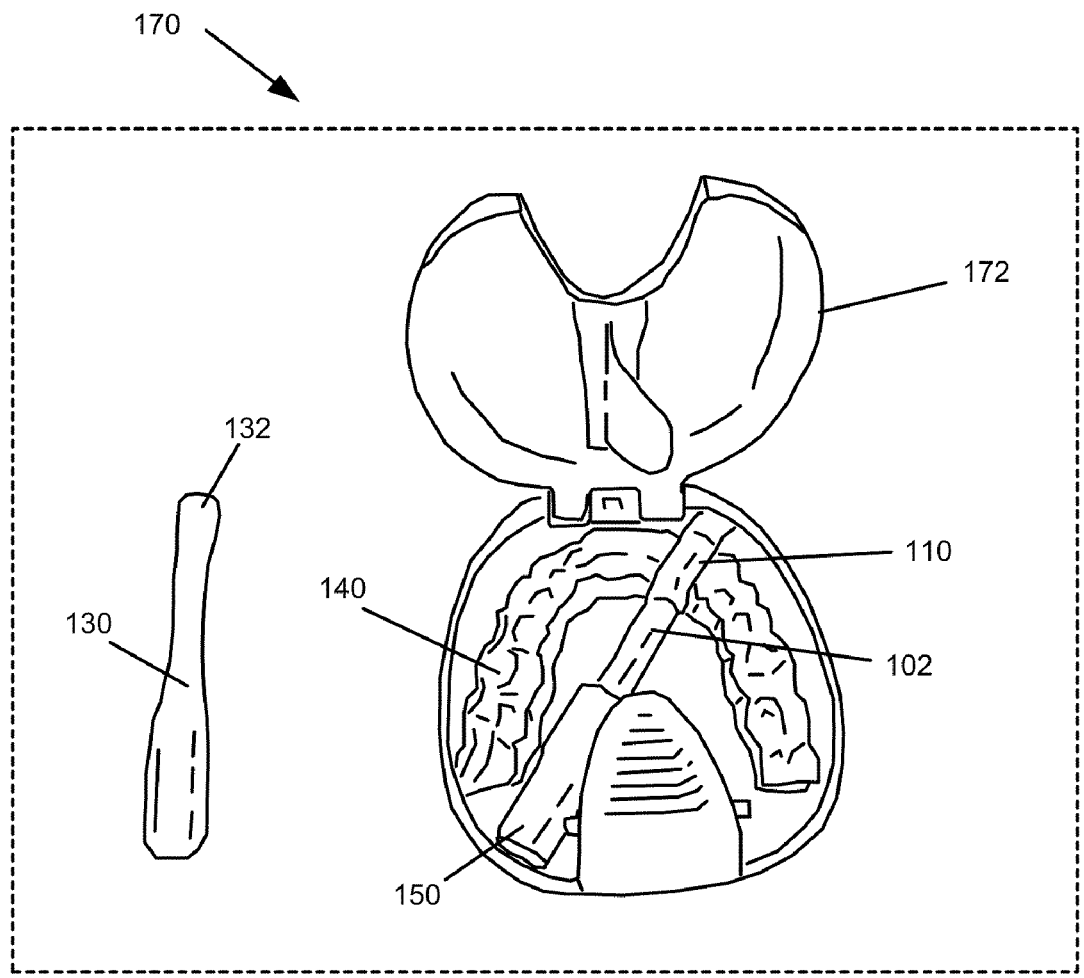
FIG. 9 shows an example orthodontic appliance kit contemplated by the present invention.

The present invention is described with reference to embodiments of the invention. Throughout the description of the invention reference is made to FIGS. 1-10.

The present invention includes an orthodontic aligner removal tool to successfully remove a patient's aligners from his or her teeth. This device is not limited to the use on plastic aligners but also in a variety of other orthodontic devices, such as retainers. However, the term aligners will be used when describing the actions of this tool. The orthodontic aligner removal tool provides patients as well as dentists and/or orthodontists many benefits which include, but are not limited to, ease of use, comfort, safety and cleanliness.

Turning to the figures, an example of an aligner removal tool 102 contemplated by the present invention is shown. The aligner removal tool 102 includes a shaft 104 having a proximate end 106 and a distal end 108. The distal end includes a handle portion 116.

The proximate end 106 includes a C-shape portion 110. The C-shaped portion 110 includes a top hook 112 and a bottom hook 114. Both hooks 112 and 114 are positioned on the same side of the tool 102, curving toward one another. Thus, the top hook 112 curves toward the bottom hook 114 and the bottom hook 114 curves toward the top hook 112. This provides safety from any sharp edges in the case of a user slipping while attempting to hook the aligner 140. The V-shaped points 118 and 120 on hooks 112 and 114 will best perform when removing the aligners 140 if they are placed between two individual teeth 142, which allows the V-shape to slide along the two teeth 142 and between the aligner 140. Preferably, top hook 112 and the bottom hook 114 are spaced at least 5 millimeters from each other along the shaft axis. In a particular embodiment, the top point 118 extends approximately six millimeters from the top inside wall of the C-shaped portion 110, and the bottom point 120 extends approximately five millimeters from the bottom inside wall of the C-shaped portion 110.

The top hook 112 serves as a mechanism to allow a patient or dentist in releasing the upper or top aligners 140 off the teeth 142. The top hook 112 extends at a greater distance from the shaft than the bottom hook 114. Preferably, the top hook 112 extends approximately ten millimeters from the back inside wall of the C-shaped portion 110, and the bottom hook 114 extends approximately six millimeters from the back inside wall of the C-shaped portion 110. This greater distance allows the user to more easily reach into the upper portion of the mouth without having the bottom of the C-shape portion 110 interfere or inhibit the user from properly hooking the top hook 112 into the small space between the orthodontic aligners 140 and teeth 142.

The depth inside of the C-shaped portion 110 allows users to gain leverage when removing the aligners. By having a curved inside radius at the top hook 112 and bottom hook 114, the user can adjust the angle of the tool toward the inside of the mouth to help hook the aligners and pull (top aligners 144) or push (bottom aligners 146) away from the teeth.

The curved inside radius of the C-shaped portion 110 allows for optimal leverage. It allows the user to roll the bottom part of the C-shaped portion 110 (when hooked into the upper aligner) under the upper set of teeth 142 if necessary, to securely hook and pop off the aligner 140.

The top hook 112 is curved toward the bottom hook 114 in order to provide a point in which the hook can fit between the aligners and users upper teeth. The top hook 112 meets the proximate end 106 of the shaft 104 at an angle less than 90 degrees. The top hook 112 includes a top V-shape tip end 118 which is configured to engage into the space between the orthodontic aligner 140 and teeth 142 when the orthodontic aligner is worn over the teeth. This is especially important when the user has a new set of aligners and they are very tightly fit over the teeth.

Once the top V-shape tip end 118 is engaged between the orthodontic device and the upper aligners, the user can pull down, setting the tool 102 more securely between the aligners and teeth. Pulling down further pops the aligners off the brackets and teeth.

The top of the C-shaped portion 110 is rounded to prevent injury to the patient's lips or gums when inserting the tool 102 into their mouth. Furthermore, having the top of the C-shaped portion 110 softly curved adds comfort and efficiency in finding the most desired position for the top and bottom hooks 112 and 114. The rounded top of the C-shaped portion 110 also adds protection when using the bottom hook 114. If the tool 102 slips in the user's mouth, the curved top will provide protection from injury to the upper portion of the user's mouth.

The bottom hook 114 serves as a mechanism to allow a patient or dentist to remove the lower or bottom aligners from the teeth. The bottom hook 114 extends from the shaft 116 at a distance less than the top hook 112. This shorter distance keeps the bottom hook 114 away from the teeth 142 when the top hook 112 is being used to pop off the upper aligners 144.

The bottom hook 114 is curved toward the top hook 112 and meets the proximate end 106 of the shaft at an angle less than 90 degrees. The bottom hook 114 includes a bottom v-shaped tip 120 which is configured to engage into the space between the orthodontic aligner 140 and teeth 142 when the orthodontic aligner is worn over the teeth. The V-shaped tip is beneficial in fitting into the tight space between the orthodontic aligner 140 and teeth 142. This is especially important when the user has a new set of aligners 140 that fit extremely tightly onto the teeth 142.

Once the bottom V-shape tip 120 is engaged between the orthodontic aligner and teeth, the user pushes up on the tool 102, thereby setting the bottom tip 120 more securely between the aligners and teeth. Further upward pressure releases the aligners from the brackets and teeth.

The bottom hook 114 also features a soften curve along the exterior bottom of the C-shaped portion 110. This provides protection from injury when the user places the tool in the lower part of his or her mouth in search of an area between the aligners 140 and teeth 142 to insert the bottom tip 120.

In addition, the users can rest the tool 102 over their bottom lip when inserting the bottom part of the C-shaped portion 110 to expose their gum line and, more importantly, the lower aligners and teeth. Having the lower lip and gum line exposed helps the user hook underneath the aligners without injuring the lower lip or gums. The bottom hook 120 also gives the user an optimal angle in removing bottom aligners from the teeth. The curved inside radius of the C-shaped portion 110, allows for optimal leverage. This lets the user roll the top part of the C-shaped portion 110 over the lower set of teeth in order to obtain the best positioning for hooking the bottom hook 114 between the lower aligners 144 and the teeth 142.

The distal end 108 of the shaft 104 includes a handle portion 116. The handle portion 116 can include a tapered end 122 opposite of the C-shaped portion 110. The handle portion 116 can include a surface treatment to aid in the gripping of the handle portion 116. At least some of the handle portion 116 can be curved away from the C-shaped portion 110 of the tool. By having the handle portion 116 curve away from the C-shaped portion 110, the user gains more leverage with the tool 102. The curve also gives users more operative space to articulate the tool 102 on the outside of their mouth.

The distal end 108 of the tool can further include a protruding portion 124 which has variety of purposes. The protruding portion 124 can assist users in gripping onto the tool 102 while popping off the orthodontic devices. Users may also attach an extension handle 130 which attaches to the orthodontic aligner tool remover. An engagement portion 134 on the extension handle 130 engages the protruding portion 124 of the handle portion 116 and locks the extension handle 130 onto the tool 102. These protruding surfaces can serve as a surface in which a user can attach a flexible sleeve 150 used in the process of setting the aligners on the teeth securely. Other devices such as a miniature toothbrush, a tooth pick, a cleaning device, a small lighting mechanism, a self supporting mechanism (to stand the tool upright on a hard surface), a loop hook could also be attached where the extension handle 130 lies.

Further, the handle portion 116 can include a tapered end 122 to allow for the flexible sleeve 150 to slide, at least partially, over the handle portion 116 and aid in seating the aligner over the teeth when the user bites down on the flexible sleeve. The extension handle 130 could also include a flexible sleeve 150 to aid in seating the aligner. The extension handle 130, when attached to the handle portion 116, allows the user to place the orthodontic aligner removal tool 102 in a toothbrush holder. This would enable users to keep the orthodontic aligner removal tool device in a convenient place for use at either the home or office.

The proximate end 106 of the tool, which includes the C-shaped portion 110 is able to function independently of the extension handle 130, if the user decides to do so. Therefore, the distal end 108 of the tool allows for a flexible sleeve 150 to be attached for assisting the user to seat their aligners. If the tool 102 does not include or the user does not attach a flexible sleeve 150, the protruding portion 124 on the distal end 108 of the handle 116 will simply serve as additional grip in articulating the C-shape portion 110 inside of the mouth when removing the aligners.

Another embodiment of the present invention is an orthodontic appliance kit 170. The kit 170 allows users to store the tool 102 with one or more orthodontic aligners 140 in a hygienic manner. The kit includes a case 172, at least one orthodontic aligner 140 for aligning teeth of a patient positioned inside the case 172, and an aligner removal tool 102 positioned inside the case 172.

The C-shaped portion 110 can be configured to fit over a portion of the orthodontic aligners 140 while in the case 172. The kit 170 may include the extension handle 130

The kit may further include a flexible sleeve 150 positioned partially over the distal end 108 of the tool 102. In one embodiment, the flexible sleeve 150 may also fit over the tapered end 132 of the extension handle 130. The extension handle 130, along with the flexible sleeve 150, are also configured to fit in the case 172.

Figure 10:
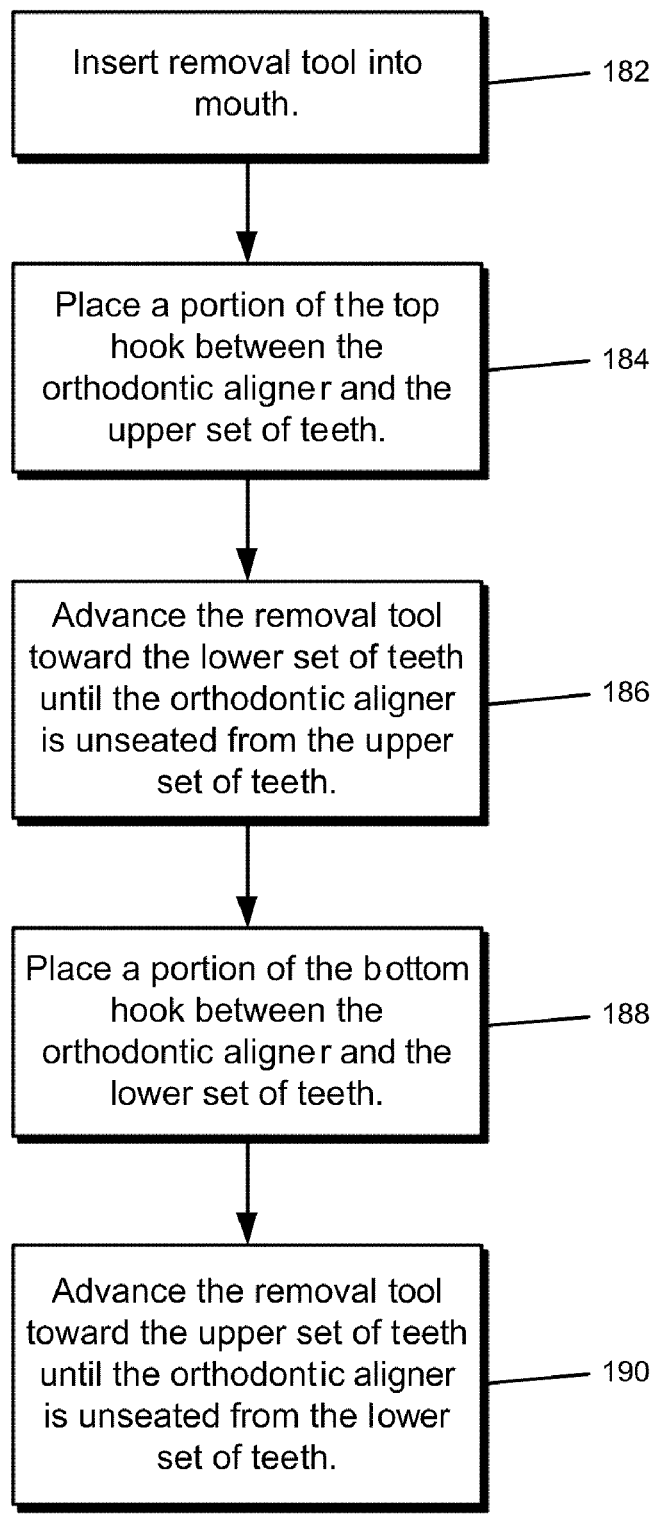
FIG. 10 is a flowchart illustrating an example method for removing orthodontic aligners in accordance with an embodiment of the present invention.

An example method for removing an orthodontic aligner 140 seated on an upper set of teeth and/or lower set of teeth is shown in FIG. 10.

The method includes an inserting step 182 for inserting the removal tool into a mouth. As discussed above, the removal tool may include a C-shaped portion having a top hook and a bottom hook. The top hook extends from a shaft and curves toward the bottom hook. Likewise, the bottom hook extends from the shaft and curves toward the top hook.

Next, at placing step 184, a portion of the top hook is placed between the orthodontic aligner and the upper set of teeth. An advancing step 186 advances the removal tool toward the lower set of teeth after placing the portion of the top hook between the orthodontic aligner and the upper set of teeth. The removal tool is advanced until the orthodontic aligner is unseated from the upper set of teeth.

Next, at placing step 188, a portion of the bottom hook is placed between the orthodontic aligner and the low set of teeth. Another advancing step 190 advances the removal tool toward the upper set of teeth after placing the portion of the bottom hook between the orthodontic aligner and the lower set of teeth. The removal tool is advanced until the orthodontic aligner is unseated from the bottom set of teeth.

While the preferred embodiments to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method for removing an orthodontic aligner seated on an upper set of teeth and lower set of teeth, the method comprising:

inserting a removal tool into a mouth, the removal tool including a C-shaped portion having a top hook and a bottom hook, the top hook extends from a shaft and curves toward the bottom hook, the bottom hook extends from the shaft and curves toward the top hook;

placing a portion of the top hook between the orthodontic aligner and the upper set of teeth;

advancing the removal tool toward the lower set of teeth after placing the portion of the top hook between the orthodontic aligner and the upper set of teeth until the orthodontic aligner is unseated from the upper set of teeth;

placing a portion of the bottom hook between the orthodontic aligner and the lower set of teeth; and advancing the removal tool toward the upper set of teeth after placing the portion of the bottom hook between the orthodontic aligner and the lower set of teeth until the orthodontic aligner is unseated from the lower set of teeth.

* * * * *